United States Patent [19]

Branca et al.

[11] 4,327,026
[45] Apr. 27, 1982

[54] BENZODIAZEPINE DERIVATIVES

[75] Inventors: Quirico Branca, Basel; Albert E. Fischli; Andre' Szente, both of Riehen, all of Switzerland

[73] Assignee: Hoffmann-La Roche Inc., Nutley, N.J.

[21] Appl. No.: 283,711

[22] Filed: Jul. 16, 1981

[30] Foreign Application Priority Data

Jul. 31, 1980 [CH] Switzerland ............... 5841/80

[51] Int. Cl.³ .......................... C07D 243/24
[52] U.S. Cl. .............. 260/239.3 D; 424/244
[58] Field of Search ................ 260/239.3 D

[56] References Cited
U.S. PATENT DOCUMENTS 4,294,758  10/1981  Fischli et al. ............... 260/239.3 D Primary Examiner—Robert T. Bond
Attorney, Agent, or Firm—Jon S. Saxe; Bernard S. Leon; Frank P. Hoffman

[57] ABSTRACT

There is presented benzodiazepine derivatives of the formula

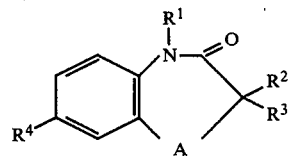

wherein A is the group

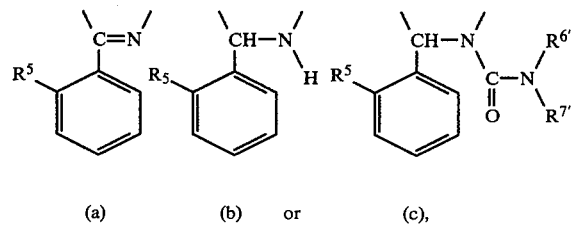

$R^1$ is lower alkyl, $R^2$ and $R^3$ each are hydrogen or lower alkyl, $R^4$ is the group

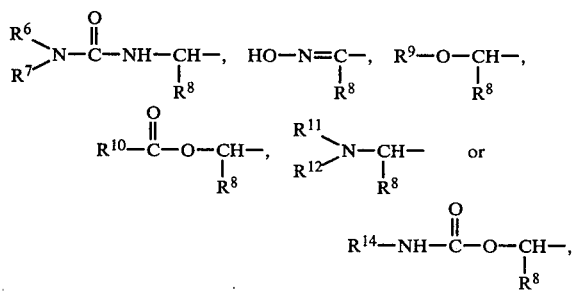

$R^5$ is hydrogen or halogen, $R^8$ is hydrogen or lower alkyl, $R^9$ is lower alkyl or lower alkoxyalkyl, $R^{10}$ is lower alkyl, $R^{11}$ is hydrogen, lower alkyl or lower hydroxyalkyl, $R^{12}$ is hydrogen or lower alkyl and $R^{14}$ is lower alkyl or aryl, and either $R^6$ is hydrogen or lower alkyl and $R^7$ is lower alkyl or lower hydroxyalkyl or $R^6$ and $R^7$ together with the nitrogen atom are a 3- to 7-membered heterocycle which, when it is at least 5-membered, can contain as a ring member an oxygen or sulphur atom or a group of the formula $>N-R^{13}$, in which $R^{13}$ is hydrogen or lower alkyl, and either $R^{6'}$ is hydrogen or lower alkyl and $R^{7'}$ is lower alkyl or $R^{6'}$ and $R^{7'}$ together with the nitrogen atom are a 3- to 7-membered heterocycle which, when it is at least 5-membered, can contain as a ring member an oxygen or sulphur atom or a group of the formula $>N-R^{13'}$, in which $R^{13'}$ is lower alkyl, with the proviso that $R^4$ is the group $R^{6'}R^{7'}N-CO-NH-CH(R^8)-$ when A is the group (c), and pharmaceutically acceptable acid addition salts thereof.

The compounds exhibit aldosterone-antagonistic properties and are suitable for the control or prevention of heart failure, hepatic ascites, primary aldosteronism and idiopathic hypertension.

12 Claims, No Drawings

BENZODIAZEPINE DERIVATIVES

DESCRIPTION OF THE INVENTION

The present invention is concerned with novel benzodiazepine derivatives of the formula

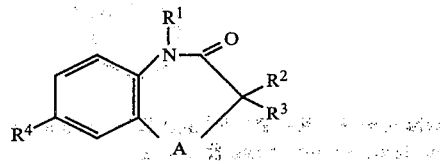

wherein A is the group

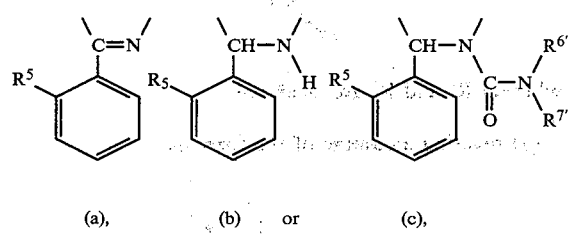

$R^5$ is hydrogen or halogen, $R^8$ is hydrogen or lower alkyl, $R^9$ is lower alkyl or lower alkoxyalkyl, $R^{10}$ is lower alkyl, $R^{11}$ is hydrogen, lower alkyl or lower hydroxyalkyl, $R^{12}$ is hydrogen or lower alkyl and $R^{14}$ is lower alkyl or aryl, and either $R^6$ is hydrogen or lower alkyl and $R^7$ is lower alkyl or lower hydroxyalkyl or $R^6$ and $R^7$ together with the nitrogen atom are a 3- to 7-membered heterocycle which, when it is at least 5-membered, can contain as a ring member an oxygen or sulphur atom or a group of the formula $>N-R^{13}$, in which $R^{13}$ is hydrogen or lower alkyl, and either $R^{6'}$ is hydrogen or lower alkyl and $R^{7'}$ is lower alkyl or $R^{6'}$ and $R^{7'}$ together with the nitrogen atom are a 3- to 7-membered heretocycle which, when it is at least 5-membered, can contain as a ring member an oxygen or sulphur atom or a group of the formula $>N-R^{13'}$, in which $R^{13'}$ is lower alkyl, with the proviso that $R^4$ is the group $R^{6'}R^{7'}N-CO-NH-CH(R^8)$—when A is the group (c), and pharmaceutically acceptable acid addition salts thereof.

Objects of the present invention are benzodiazepine derivatives of the foregoing formula I and their pharmaceutically acceptable acid addition salts per se and as pharmaceutically active substances, the manufacture of these compounds and intermediates for the manufacture of these compounds, medicaments containing one or more compounds of general formula I or pharmaceutically acceptable acid addition salts thereof, and the manufacture of such medicaments, as well as the use of benzodiazepine derivatives of formula I and of pharmaceutically acceptable acid addition salts thereof in the control or prevention of illnesses.

The term "lower alkyl", alone or in combinations such as in "lower hydroxyalkyl", "lower alkoxyalkyl" and the like denotes straight-chain or branched-chain saturated hydrocarbon groups containing at most 7, preferably at most 4, carbon atoms such as methyl, ethyl, n-propyl, isopropyl, n-butyl, t-butyl etc. The term "lower hydroxyalkyl" includes groups such as 2-hydroxyethyl, 3-hydroxy-2-propyl and the like. The term "lower alkoxyalkyl" includes groups such as methoxymethyl, ethoxymethyl, methoxy-2-propyl and the like. The term "halogen" signifies fluorine, chlorine, bromine or iodine. The term "aryl" signifies phenyl optionally substituted by lower alkyl, halogen, nitro or lower alkoxy. When $R^6$ and $R^7$ together with the nitrogen atom signify a 3- to 7-membered heterocycle, then there primarily come into consideration aziridine, pyrrolidine, piperidine, morpholine and piperazine groups.

In one special aspect, the present invention includes compounds of the above formula I in which either $R^1$ and $R^2$ both are methyl or $R^1$ is ethyl and $R^2$ is hydrogen when $R^3$ is hydrogen, $R^4$ is the group $HO-N=C(CH_3)-$, A is the group (a) and $R^5$ is flourine. In a further special aspect, the present invention includes compounds of the above formula I in which $R^2$ and $R^3$ both are lower alkyl when A is the group (a), $R^4$ is the group $HO-N=C(R^8)-$ and $R^5$ and $R^8$ are as above.

Among the compounds of formula I there are preferred those in which A is the group (a) or (b). $R^1$ preferably is methyl or ethyl. $R^2$ and $R^3$ preferably are hydrogen or methyl. $R^4$ preferably is the group $R^6R^7N-CO-NH-CH(R^8)-$, $HO-N=C(R^8)-$, $R^9-O-CH(R^8)-$ or $R^{11}R^{12}N-CH(R^8)-$. $R^5$ preferably is hydrogen or fluorine. Preferably, $R^6$ and $R^7$ both are methyl, or $R^6$ is hydrogen and $R^7$ is n-butyl or hydroxyethyl, or $R^6$ and $R^7$ together with the nitrogen atom are pyrrolidinyl. $R^8$ preferably is hydrogen or methyl. $R^9$ preferably is methoxymethyl. $R^{10}$ preferably is methyl. Preferably, $R^{11}$ and $R^{12}$ both are hydrogen or both are methyl, or $R^{11}$ is hydroxyethyl and $R^{12}$ is hydrogen.

Especially preferred compounds of formula I are:
1-Ethyl-5-(o-fluorophenyl)-1,3-dihydro-7-[1-(methoxymethoxy)ethyl]-2H-1,4-benzodiazepin-2-one;
1-ethyl-5-(o-fluorophenyl)-1,3,4,5-tetrahydro-7-[1-(hydroxyimino)ethyl]-2H-1,4-benzodiazepin-2-one;
1-ethyl-5-(o-fluorophenyl)-1,3,4,5-tetrahydro-7-/1-[(2-hydroxyethyl)amino]ethyl/-2H-1,4-benzodiazepin-2-one;
7-[1-(dimethylamino)ethyl]-1-ethyl-5-(o-fluorophenyl)-1,3,4,5-tetrahydro-2H-1,4-benzodiazepin-2-one;
7-(1-aminoethyl)-5-(o-fluorophenyl)-1,3-dihydro-1,3-dimethyl-2H-1,4-benzodiazepin-2-one and
1-[(2,3-dihydro-1-methyl-2-oxo-5-phenyl-1H-1,4-benzodiazepin-7-yl)methyl]-3-(2-hydroxyethyl)urea.

The novel benzodiazepine derivatives of general formula I and their pharmaceutically acceptable acid addition salts can be manufactured in accordance with the invention by (a) reducing a nitrile of the formula

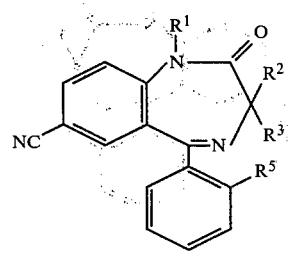

wherein $R^1$, $R^2$, $R^3$ and $R^5$ are as above,
to the corresponding primary amine,
or (b) treating a carbonyl compound of the formula

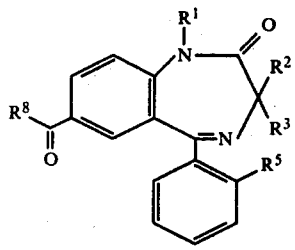

III wherein $R^1$, $R^2$, $R^3$, $R^5$ and $R^8$ are as above,
with hydroxylamine,
or (c) reacting a carbonyl compound of the above formula III with an amine of the formula

IV wherein $R^{11}$ and $R^{12}$ are as above,
and a reducing agent,
or (d) monoalkylating or dialkylating the primary amino group in a compound of the formula

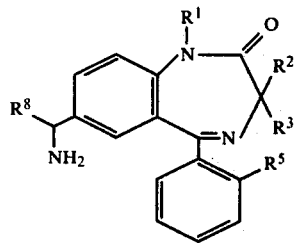

Ib' wherein $R^1$, $R^2$, $R^3$, $R^5$ and $R^8$ are as above,
or (e) reducing an oxime of the formula

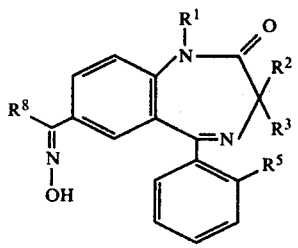

Ia wherein $R^1$, $R^2$, $R^3$, $R^5$ and $R^8$ are as above,
to the corresponding primary amine,
or (f) reacting an isocyanate of the formula

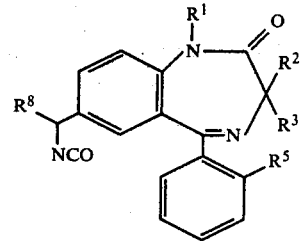

V wherein $R^1$, $R^2$, $R^3$, $R^5$ and $R^8$ are as above,
with an amine of the formula

VI wherein $R^6$ and $R^7$ are as above,
or (g) reacting an amine of the formula

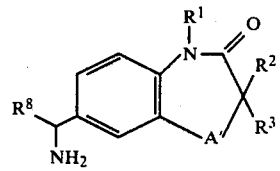

Ib wherein A' is the group (a)
or (b) and $R^1$, $R^2$, $R^3$ and $R^8$ are as above,
with a halide of the formula

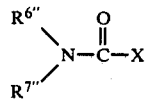

VII wherein X is halogen, and either $R^{6''}$ and $R^{7''}$ each are lower alkyl or $R^{6''}$ and $R^{7''}$ together with the nitrogen atom are a 3- to 7-membered heterocycle which, when it is at least 5-membered, can contain as a ring member an oxygen or sulphur atom or a group of the formula $>N-R^{13'}$, in which $R^{13'}$ is lower alkyl,
or (h) reacting an amine of the above formula Ib with an isocyanate of the formula

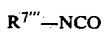

$R^{7'''}$—NCO

VIII wherein $R^{7'''}$ is lower alkyl,
or (i) etherifying an alcohol of the formula

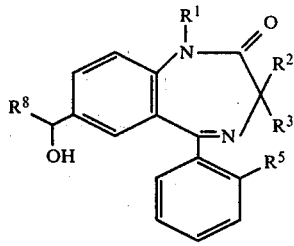

IX wherein $R^1$, $R^2$, $R^3$, $R^5$ and $R^8$ are as above,
with a compound of the formula $$R^9—L \qquad \text{X}$$

wherein $R^9$ is as above and L is a leaving group,
or (j) reacting an alcohol of the above formula IX with an agent which yields a group of the formula

  XI wherein $R^{10}$ is as above,
or (k) reacting an alcohol of the above formula IX with an isocyanate of the formuls $$R^{14}—NCO \qquad \text{XII}$$

wherein $R^{14}$ is as above,
or (l) reducing an imino compound of the formula

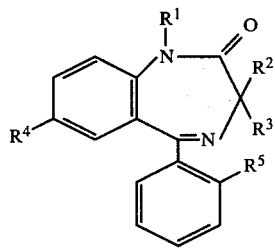  Ic wherein $R^1$, $R^2$, $R^3$, $R^4$ and $R^5$ are as above,
to the corresponding amine,
or (m) converting a compound of formula I into a pharmaceutically acceptable acid addition salt.

In accordance with embodiment (a) of the process benzodiazepine derivatives of formula I can be manufactured by reducing a nitrile of formula II to the corresponding primary amine. It will be appreciated that, depending on the reactivity of the reducing agent which is used, not only the nitrile group but also the imino group which is present in the molecule can be reduced to the corresponding amino group in the same operation. If the reduction is carried out, for example, using elemental hydrogen in the presence of a catalyst which is not particularly reactive (e.g. Raney-nickel) in an ammonia-containing alcohol (e.g. methanol or ethanol) and at temperatures of about room temperature to about 70° C., preferably ca 50° C., and pressures of about normal pressure to about 6 atmospheres, preferably at 3.5 atmospheres, then, depending on the duration of the reduction, the nitrile group can be selectively reduced to the primary amine. If the reduction is continued after the uptake of one equivalent of hydrogen, then the imino group which is present in the molecule is also reduced to the amine.

In accordance with embodiment (b) of the process, benzodiazepine derivatives of formula I can be manufactured by treating a compound of formula III with hydroxylamine. This treatment can be carried out according to various methods which are generally usual and familiar to any person skilled in the art. In a preferred aspect, compounds of formula III are treated with hydroxylamine hydrochloride in pyridine or in a mixture of pyridine and an alcohol such as, for example, methanol or ethanol, conveniently at room temperature.

In accordance with embodiment (c) of the process, benzodiazepine derivatives of formula I can be manufactured by reacting a compound of formula III with an amine of formula IV and a reducing agent. For example, compounds of formula III can be reacted with an amine of formula IV and a reducing agent such as sodium cyanoborohydride in an alcohol such as, for example, methanol or ethanol which contains an acid such as, for example, hydrochloric acid. In a first step there is formed from the carbonyl compound of formula III and the amine of formula IV the corresponding imine which is then reduced to the amine in the second step. It will be appreciated that the imino group originally present in the molecule is likewise reduced to the corresponding amine.

In accordance with embodiment (d) of the process, benzodiazepine derivatives of formula I can be manufactured by monoalkylating or dialkylating the primary amino group in an amine of formula Ib'. This alkylation can be carried out using any suitable alkylating agent; for example, using a corresponding halide such as methyl iodide, 2-bromoethanol, iodoethane and the like, using a dialkyl sulphate such as, for example, dimethyl sulphate or diethyl sulphate in the presence of an acid-binding agent, using an aldehyde such as, for example, formaldehyde and acetaldehyde under reducing conditions or using a corresponding epoxy compound such as ethylene oxide and the like.

The alkylation conditions can be chosen readily by any person skilled in the art depending on the alkylating agent which is used. For example, an amine of formula Ib' is heated to boiling under reflux with an equivalent amount of aldehyde in formic acid until carbon dioxide no longer evolves, whereupon the solvent is removed in vacuo and the free base is isolated by neutralisation.

In accordance with embodiment (e) of the process, benzodiazepine derivatives of formula I can be manufactured by reducing an oxime of formula Ia to the corresponding primary amine. This reduction is carried out according to generally usual methods which are customary to any person skilled in the art; it being appreciated that, depending on the reducing agent which is used, the imino group which is present in the molecule can also be reduced.

If the reduction is carried out, for example, in an alcohol such as, for example, methanol or ethanol, which contains ammonia, using elemental hydrogen as the reducing agent and Raney-nickel as the catalyst, then the oxime group can be selectively reduced to the amine by working at room temperature and normal pressure and discontinuing the reduction after the uptake of one equivalent of hydrogen.

In accordance with embodiment (f) of the process, benzodiazepine derivatives of formula I can be manufactured by reacting an isocyanate of formula V with an amine of formula VI. In this case, the benzodiazepine derivative of formula V intended for use is conveniently prepared in the manner described below from a corresponding benzodiazepine derivative of formula Ib' shortly or immediately before the reaction with the amino compound of formula VI and is introduced into the reaction not in isolated form but in the solution in which it has previously been prepared from the corresponding benzodiazepine derivative of formula Ib'.

An amino compound of formula VI can then be added to the aforementioned solution containing the benzodiazepine derivative of formula V. In so doing, the amino compound of general formula VI can be used in the form of a solution or also in the absence of a solvent. Where an amino compound which is gaseous at room temperature is used (e.g. in the case of methylamine), it can be introduced as the gas into the aforementioned solution containing the benzodiazepine derivative of formula V.

On the other hand, it is also possible to add the aforementioned solution containing the benzodiazepine derivative of formula V to the amino compound of formula VI, conveniently in the form of a solution.

In many cases it is convenient to use an excess of the amino compound of formula VI and this is indeed necessary when it contains more than 1 nitrogen atom which is capable for the reaction with an isocyanate group (e.g. in the case of piperazine).

Various organic solvents which are inert under the reaction conditions (e.g. halogenated hydrocarbons such as dichloroethane, methylene chloride, chloroform, o-dichlorobenzene etc., ethers such as tetrahydrofuran, dioxan, dimethoxyethane, diethyleneglycol, dimethyl ether etc. or the like) are suitable as the solvent for embodiment (f) of the process.

The reaction of the compounds of formulae V and VI is conveniently carried out at room temperature or at a temperature below room temperature.

When the amino compound of formula VI is added to a solution of the benzodiazepine derivative of formula V the addition should be performed within a short time, whereas in the opposite case (i.e. when the solution of the benzodiazepine derivative of formula V is added to the amino compound of formula VI) the promptness with which the addition is carried out is not critical.

In accordance with embodiment (g) of the process, benzodiazepine derivatives of formula I are manufactured by reacting an amine of formula Ib with a halide of formula VII. This reaction is carried out in the presence of an acid-binding agent; for example, an inorganic base such as potassium carbonate, sodium carbonate etc. or an organic base such as a tertiary amino compound (e.g. triethylamine, N-ethyl-diisopropylamine, quinuclidine etc.). The reaction is conveniently carried out at room temperature or at a temperature below room temperature. The reaction proceeds fairly slowly and generally lasts several days.

Of course, in compounds of formula Ib in which A' signifies the group (b), both amino groups present in the molecule react with the carbamoyl halide of formula VII, so that at least two equivalents of the latter must be used.

In accordance with embodiment (h) of the process, benzodiazepine derivatives of formula I are manufactured by reacting an amine of formula Ib with an isocyanate of formula VIII. This reaction is conveniently carried out in an organic solvent which is inert under the reaction conditions; for example, in a halogenated hydrocarbon such as methylene chloride, dichloroethane, chloroform, o-dichlorobenzene etc., in an ether such as tetrahydrofuran, dioxan, dimethoxyethane, diethyleneglycol dimethyl ether etc. or the like. In many cases it has been found to be favourable to carry out the reaction in the presence of a catalytically-active small amount of a base; for example, in the presence of a tertiary amino compound such as triethylamine, N-ethyldiisopropylamine, quinuclidine etc. The temperature is not critical for the reaction of the compounds of formulae Ib and VIII, and the reaction can therefore be carried out at room temperature or at a temperature below or above room temperature (e.g. at the reflux temperature).

Of course, in compounds of formula Ib in which A' is the group (b), both amino groups present in the molecule react with the isocyanate of formula VIII, so that at least two equivalents of the latter must be used.

In accordance with embodiment (i) of the process, benzodiazepine derivatives of formula I can be manufactured by etherifying an alcohol of formula IX with a compound of formula X. The leaving group denoted by L in compounds of formula X can be a halogen atom such as, for example, chlorine, bromine or iodine, or a sulphonic acid group such as, for example, p-toluenesulphonyloxy, methanesulphonyloxy or p-bromobenzenesulphonyloxy, or a quaternary ammonium group such as, for example, the trimethylammonium group, or any equivalent leaving group. Compounds such as, for example, dimethyl sulphate and diethyl sulphate are likewise included within formula X. Other suitable alkylating agents are, for example, methyl iodide, ethyl bromide, chlorodimethyl ether and the like.

Usually, the etherification is carried out in an organic solvent which is inert under the reaction conditions (e.g. an ether such as tetrahydrofuran, dioxan, dimethoxyethane, and the like) in the presence of an acid-binding agent (e.g. sodium carbonate, potassium carbonate, triethylamine, quinuclidine, etc.). In a preferred aspect, a basic solvent such as, for example, dimethylaniline, pyridine, triethylamine and the like is used.

In accordance with embodiment (j) of the process, benzodiazepine derivatives of formula I can be manufactured by reacting an alcohol of formula IX with an agent which yields a group of formula XI, i.e. by acylating an alcohol of formula IX to the corresponding ester. The acylating agent can be a corresponding acid halide, acid anhydride acid imidazolide or mixed anhydride (e.g. with mesitylene sulphonic acid, trifluoroacetic acid and the like) or the corresponding free acid in combination with a condensing agent such as, for example, dicyclohexylcarbodiimide, thionyldiimidazole, 2-chloro-1-methyl-pyridinium iodide and the like.

The reaction conditions can be readily chosen by any person skilled in the art depending on the acylating agent which is used. For example, an alcohol of general formula IX can be reacted with an anhydride such as, for example, acetic anhydride in a basic organic solvent such as, for example, pyridine, the reaction conveniently being carried out at room temperature, although it can be carried out at a temperature below or above room temperature.

In accordance with embodiment (k) of the process, benzodiazepine derivatives of formula I can be manufactured by reacting an alcohol of formula IX with an isocyanate of formula XII. This reaction is carried out in analogy to the reaction of compounds of formula Ib with isocyanates of formula VIII in accordance with embodiment (g) of the process. Having regard to the lesser reactivity of alcohols in comparison to amines, the reaction is preferably carried out at an elevated temperature (e.g. the boiling point of the reaction mixture) and conveniently extends the reaction time.

In accordance with embodiment (l) of the process, benzodiazepine derivatives of formula I can be manufactured by reducing an imino compound of formula Ic to the corresponding amine. Sodium cyanoborohydride is an example of a reducing agent which is suitable for this embodiment of the process. For example, the reduction is carried out in methanol under controlled, weakly acidic conditions, so that the imino group present in the molecule is selectively reduced to the corresponding amine.

In accordance with embodiment (m) of the process, benzodiazepine derivatives of formula I are converted into their pharmaceutically acceptable acid addition salts. There come into consideration not only salts with pharmaceutically acceptable inorganic acids such as, for example, hydrogen chloride, hydrogen bromide, sulphuric acid, phosphoric acid and the like, but also salts with pharmaceutically acceptable organic acids such as, for example, citric acid, acetic acid, succinic acid, methanesulphonic acid, p-toluenesulphonic acid and the like. The manufacture of such salts is carried out according to methods which are generally usual and familiar to any person skilled in the art.

The benzodiazepine derivatives of formula II used as starting materials in embodiment (a) of the process belong to a class of compound which is known per se and many specific representatives of this class of compound have already been described in the literature. Representatives which have not previously been specifically described can be prepared according to known methods which are familiar to any person skilled in the art. Various Examples hereinafter contain detailed information concerning the manufacture of certain compounds of formula II.

Nitriles of formula II can be prepared, for example, starting from nitrobenzophenone derivatives of formula XIII in accordance with the following Reaction Scheme in which $R^1$, $R^2$, $R^3$ and $R^5$ are as above:

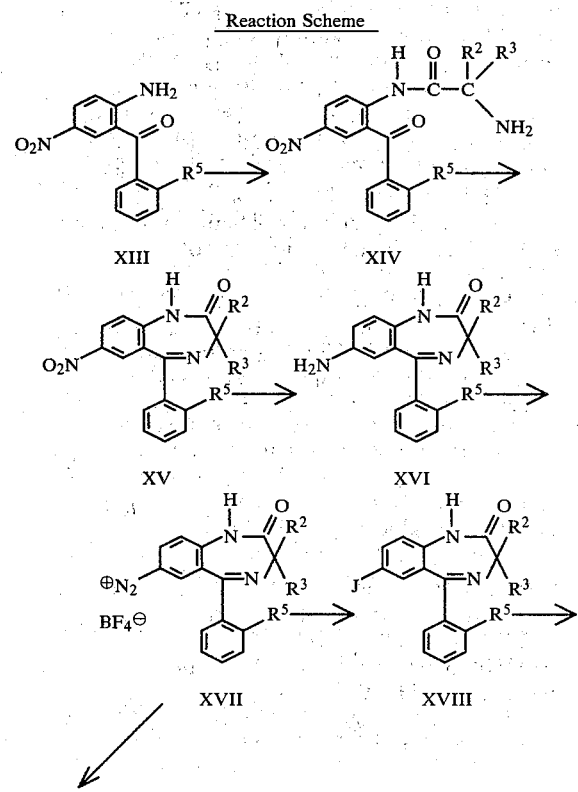

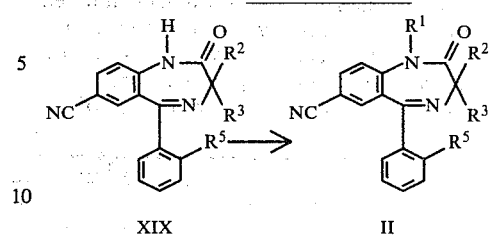

The carbonyl compounds of formula III used as starting materials in embodiment (b) of the process belong to a known class of compound and can be prepared according to generally known methods which are familiar to any person skilled in the art; for example, starting from nitriles of formula II. By treating such nitriles with a lower alkyl lithium in an inert organic solvent there are obtained selectively the corresponding 7-alkanoyl-benzodiazepine derivatives of formula III.

Some of the Examples hereinafter contain detailed information concerning the preparation of certain compounds of formula III.

The isocyanates of formula V used as starting materials in embodiment (f) of the process can be prepared, as mentioned above, from corresponding benzodiazepine derivatives of formula Ib', namely by reaction with phosgene. In this case, conveniently a solution of phosgene in an organic solvent which is inert under the reaction conditions is prepared and then while cooling a solution of a benzodiazepine derivative of formula Ib' is added thereto, the mixture is thereupon heated to boiling under reflux for some time, then cooled and finally the resulting solution is made basic or at least neutral with a tertiary organic amino compound such as, for example, triethylamine. A thus-obtained solution of an isocyanate of formula V can be stored for several hours with the exclusion of moisture and in the cold. As mentioned earlier, the solution is processed directly without isolating the isocyanate of formula V contained therein.

The isocyanates of formula V are also an object of the present invention.

The alcohols of formula IX used as starting materials in embodiment (i) of the process belong to a class of compound which is known per se. Representatives which have not previously been specifically described can be prepared according to methods which are known and familiar to any person skilled in the art. The preparation of certain compounds of formula IX is described in some of the following Examples.

Carbonyl compounds of formula III are conveniently used as starting materials for the manufacture of compounds of formula IX. By selectively reducing the carbonyl group there are obtained the corresponding alcohols of formula IX. In this case it will be appreciated that there can be used only those reducing agents which do not attack amide or imino groups which are also present in the molecule. Sodium borohydride is an example of a reducing agent which is especially suitable for this purpose.

Surprisingly, it has been shown that the benzodiazepine derivatives of formula I hereinbefore display no or only very slight activities on the central nervous system, whereas they exhibit pronounced aldosterone-antagonistic properties. These aldosterone-antagonistic properties can be demonstrated in adrenalectomised rats as illustrated hereinafter.

If aldosterone is administered to adrenalectomised rats, then there is observed, in comparison to untreated animals, a pronounced reduction of the sodium excretion (sodium retention), an increased potassium excretion (potassium excretion) as well as a reduction of the excreted urine volume. If compounds of formula I are administered to the animals before the treatment with aldosterone, then there is observed, in comparison to animals which are treated only with aldosterone (control animals), a pronounced increase of the sodium excretion (i.e. the sodium retention caused by aldosterone is antagonised), whereas the potassium excretion and the urine volume are influenced to a lesser extent.

The standard experiment is carried out as follows:

Female Holtzmann rats (150–180 g) are bilaterally adrenalectomised 70 to 74 hours before the beginning of the experiment. After the operation, the animals receive a customary rat dry feed and 0.9% sodium chloride solution for drinking. 16–17 hours before the beginning of the experiment the feed is removed from the animals, but they can subsequently drink, as before, 0.9% sodium chloride solution ad libitum. At the beginning of the experiment the substance to be tested as an aldosterone-antagonist is administered to the animals by means of a stomach probe. 30 minutes later the animals receive a subcutaneous injection of 4 mmg/kg of aldosterone. After a further 90 minutes, the urinary bladders of the animals are emptied by careful suprapubic pressure, whereupon the animals are placed individually in metabolic cages without food and without drink. The urine of the animals is then collected for 3 hours, whereupon their urinary bladders are once more emptied. The spontaneously excreted urine and the remaining urine obtained at the conclusion of the experiment by pressing-out the urinary bladders are collected in graduated centrifuge glasses. Sodium and potassium concentrations in the urine are determined with a flame photometer.

The following Table contains results obtained in the previously described experiment with representative compounds of formula I. In this Table there are given for each of the compounds in question the dosage administered (in mg/kg p.o.) as well as the percentage variation in the urine volume, the sodium excretion and the potassium excretion in comparison with the control animals (i.e. in comparison with the animals treated only with aldosterone). Moreover, the Table contains data concerning the acute toxicity of the compounds investigated (LD 50 in mg/kg in the case of single oral administration to mice).

TABLE

Toxicity and activity in adrenalectomised rats

| $R^1$ | $R^2$ | $R^3$ | A | $R^5$ | $R^4$ | Dosage mg/kg p.o. | Volume in %, | [Na$^+$] based on | [K$^+$] control animals | LD 50 mg/kg p.o. |
|---|---|---|---|---|---|---|---|---|---|---|
| Et | H | H | $R^5$-phenyl-C(=N-)- | F | $CH_3-O-CH_2-O-CH(CH_3)-$ | 1 | 138 | 359 | 93 | 500 |
| Et | H | H | $R^5$-phenyl-CH(-NH-)- | F | $HO-N=C(CH_3)-$ | 1 | 157 | 247 | 87 | >5000 |
| Et | H | H | $R^5$-phenyl-CH(-NH-)- | F | $HO-(CH_2)_2-NH-CH(CH_3)-$ | 1 | 150 | 306 | 93 | 4000 |
| Et | H | H | $R^5$-phenyl-CH(-NH-)- | F | $(CH_3)_2-N-CH(CH_3)-$ | 1 | 147 | 252 | 90 | 500 |
| $CH_3$ | $CH_3$ | H | $R^5$-phenyl-C(=N-)- | F | $H_2N-CH(CH_3)-$ | 1 | 169 | 298 | 102 | 625 |
| $CH_3$ | H | H | $R^5$-phenyl-C(=N-)- | H | $HO-(CH_2)_2-NH-CO-CH_2-NH-$ | 1 | 130 | 224 | 82 | >5000 |

The benzodiazepine derivatives of formula I and their pharmaceutically acceptable acid addition salts can be used as medicaments, for example, in the form of pharmaceutical preparations. The pharmaceutical preparations can be administered orally, for example, in the form of tablets, coated tablets, dragées, hard and soft gelatin capsules, solutions, emulsions or suspensions. The administration can, however, also be carried out rectally (e.g. in the form of suppositories) or parenterally (e.g. in the form of injection solutions).

For the manufacture of tablets, coated tablets, dragees and hard gelatin capsules, the benzodiazepine derivatives of formula I and their pharmaceutically acceptable acid addition salts can be processed with pharmaceutical inert, inorganic or organic excipients. Examples of such excipients which can be used for tablets, dragees and hard gelatin capsules are lactose, maize starch or derivatives thereof, talc, stearic acid or its salts etc.

Suitable excipients for soft gelatin capsules are, for example, vegetable oils, waxes, fats, semi-solid and liquid polyols etc. Depending on the nature of the active substance no excipients are, however, generally necessary in the case of soft gelatin capsules.

Suitable excipients for the manufacture of solutions and syrups are, for example, water, polyols, saccharose, invert sugar, glucose and the like.

Suitable excipients for injection solutions are, for example, water, alcohols, polyols, glycerine, vegetable oils etc.

Suitable excipients for suppositories are, for example, natural or hardened oils, waxes, fats, semiliquid or liquid polyols and the like.

Moreover, the pharmaceutical preparations can contain preserving agents, solubilising agents, stabilising agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned hereinbefore, medicaments containing one or more compounds of formula I or pharmaceutically acceptable acid addition salts thereof are also an object of the present invention as is a process for the manufacture of such medicaments which is characterised by bringing one or more compounds of formula I or pharmaceutically acceptable acid addition salts thereof and, if desired, one or more other therapeutically valuable substances into a galenical administration form. A further object of the present invention is, as mentioned hereinbefore, the use of benzodiazepine derivatives of formula I and of pharmaceutically acceptable acid addition salts thereof in the control or prevention of illnesses, especially in the control or prevention of heart failure, of hepatic ascites, of primary aldosteronism and of adiopathic hypertension. The dosage can vary within wide limits and is, of course, adjusted to the individual requirements in any particular case. In general, in the case of oral administration a daily dosage of about 20 mg to about 1500 mg should be appropriate.

In the following Examples which illustrate the present invention in more detail but are not intended to limit its extent, all temperatures are given in degrees Centigrade.

EXAMPLE 1

(a) A solution of 105.6 g (0.47 mol) of carbobenzoxy-DL-alanine in 830 ml of tetrahydrofuran is treated dropwise at 0° with 41.5 ml (68.1 g; 0.57 mol) of thionyl chloride, the mixture is subsequently stirred at room temperature for 1 hour, treated with a solution of 100 g (0.38 mol) of 2-amino-2'-fluoro-5-nitrobenzophenone in 580 ml of tetrahydrofuran and stirred at room temperature for 24 hours. After concentrating the mixture in vacuo, the residue is taken up in 1.8 l of methylene chloride/ethanol (9:1), this solution is treated with 1.0 l of 1 N potassium bicarbonate solution and stirred for 30 minutes. The aqueous phase is separated and extracted with 1.6 l of methylene chloride. The combined organic phases are washed with water, dried and evaporated.

(b) The above crude intermediate is taken up in 750 ml of 33 percent hydrobromic acid in glacial acetic acid and vigorously stirred at room temperature for 5 hours. The mixture is subsequently evaporated in vacuo and the residue is partitioned between 3 l of water and 3 l of ether. The aqueous phase is separated, neutralised with 105 g of solid potassium carbonate and extracted with methylene chloride. After washing with water, the organic phase is dried and evaporated.

(c) The thus-obtained crude intermediate is dissolved in 1.5 l of toluene and 150 ml of glacial acetic acid and heated to boiling under reflux for 7 hours on a water-separator. Subsequently, the solution is evaporated to dryness in vacuo and traces of acetic acid are removed by azeotropic evaporation with toluene. The crude 5-(o-fluorophenyl)-1,3-dihydro-3-methyl-7-nitro-2H-1,4-benzodiazepin-2-one is further processed without additional purification.

(d) 62.7 g (0.2 mol) of crude rac-5-(o-fluorophenyl)-1,3-dihydro-3-methyl-7-nitro-2H-1,4-benzodiazepin-2-one in 1 l of concentrated hydrochloric acid is treated portionwise while stirring with a total of 135.5 g (0.6 mol) of tin chloride, stirred at room temperature for 2 hours and the mixture is neutralised in the cold with 10 N sodium hydroxide. The aqueous phase is extracted with a total of 8 l of methylene chloride/ethanol (4:1), the combined organic extracts are washed with saturated sodium chloride solution, dried and evaporated. From ether there is obtained 7-amino-5-(o-fluorophenyl)-1,3-dihydro-3-methyl-2H-1,4-benzodiazepin-2-one of melting point 270°.

(e) A solution of 24.2 g (85.4 mmol) of 7-amino-5-(o-fluorophenyl)-1,3-dihydro-3-methyl-2H-1,4-benzodiazepin-2-one in 100 ml of water and 200 ml of 50 percent aqueous hydrofluoboric acid is treated dropwise while stirring at 0° with a solution of sodium nitrite (93.96 mmol) in 15 ml of water so that the sodium nitrite solution enters below the surface of the mixture (addition time: 30 minutes). The mixture is subsequently stirred at 5° for a further 1 hour and then left to stand at −20°. The cyrstallised-out material is filtered off, washed with cold isopropanol and cold ether and dried in vacuo at room temperature. There is thus obtained 5-(o-fluorophenyl)-2,3-dihydro-3-methyl-2-oxo-1H-1,4-benzodiazepine-7-diazonium tetrafluoroborate.

(f) 33.0 g of iodine are added to a solution, which is stirred at room temperature and with the exclusion of light, of 32.65 g of the above diazonium salt and 0.918 g of 18-crown-6 in 700 ml of chloroform, the mixture is stirred for a few minutes and 7.9 g of potassium acetate are added thereto. The mixture is stirred at room temperature for 20 hours, filtered, washed with 10 percent sodium bisulphite solution and four times with water, dried and evaporated. The residue is filtered over 250 g of silica gel while washing with chloroform. From cyclohexane there is obtained 5-(o-fluorophenyl)-1,3-dihydro-7-iodo-3-methyl-2H-1,4-benzodiazepin-2-one of melting point 211°.

(g) 23.2 g (58.8 mmol) of 5-(o-fluorophenyl)-1,3-dihydro-7-iodo-3-methyl-2H-1,4-benzodiazepin-2-one and 10 g (0.11 mol) of copper (I) cyanide in 250 ml of dimethylformamide are heated at 150° for 2 hours under argon. After cooling, 700 ml of water are added to the mixture and the resulting precipitate is filtered off. This is dissolved in 1 l of water/ethylenediamine (1:1) and extracted with 1 l of methylene chloride; the separated aqueous phase is extracted a further twice with methylene chloride. The combined organic extracts are washed with water, dried and evaporated. The residue gives, from cyclohexane, 5-(o-fluorophenyl)-2,3-dihydro-3-methyl-2-oxo-1H-1,4-benzodiazepine-7-carbonitrile of melting point 216°.

(h) 110 ml of a 2 N solution of methyl lithium in ether are added dropwise to a solution, stirred at −70° under argon, of 12.81 g (43.68 mmol) of 5-(o-fluorophenyl)-2,3-dihydro-3-methyl-2-oxo-1H-1,4-benzodiazepine-7-carbonitrile in 500 ml of tetrahydrofuran. After 21 hours at −70°, 440 ml of 2 N hydrochloric acid are added thereto at −70° and, after warming to room temperature, the mixture is neutralised with 135 ml of 3 N sodium hydroxide. After separating the aqueous phase, the organic phase is evaporated at 40° in vacuo, the residue is taken up in methylene chloride and the organic phase is washed with the aqueous phase separated above. The methylene chloride solution is washed with water, dried and evaporated. The residue yields, from methylene chloride/cyclohexane, 7-acetyl-5-(o-fluorophenyl)-1,3-dihydro-3-methyl-2H-1,4-benzodiazepin-2-one of melting point 203°.

(i) 7.15 g of potassium carbonate are added to a solution of 7.15 g (23.04 mmol) of 7-acetyl-5-(o-fluorophenyl)-1,3-dihydro-3-methyl-2H-1,4-benzodiazepin- 2-one and 15 ml of methyl iodide in 300 ml of acetone and the mixture is stirred at room temperature for 21 hours. The insoluble material is filtered off and the solution is evaporated in vacuo. The residue is taken up in methylene chloride, washed with water, dried and evaporated. From cyclohexane there is obtained 7-acetyl-5-(o-fluorophenyl)-1,3-dihydro-1,3-dimethyl-2H-1,4-benzodiazepin-2-one of melting point 65°.

(j) A solution of 4.41 g (13.60 mmol) of 7-acetyl-5-(o-fluorophenyl)-1,3-dihydro-1,3-dimethyl-2H-1,4-benzodiazepin-2-one and 4.41 g (63.46 mmol) of hydroxylamine hydrochloride in 250 ml of pyridine is stirred at room temperature for 19 hours, subsequently poured on to ice and extracted with chloroform. The organic extracts are washed successively with 2 N hydrochloric acid and water, dried and evaporated. After chromatography of the residue on 250 g of silica gel using chloroform/ethanol (98:2) as the elution agent, there is obtained 5-(o-fluorophenyl)-1,3-dihydro-7-[1-(hydroxyimino)ethyl]-1,3-dimethyl-2H-1,4-benzodiazepin-2-one of melting point 101°–103°.

EXAMPLE 2

A solution of 4.1 g (12.08 mmol) of 5-(o-fluorophenyl)-1,3-dihydro-7-[1-(hydroxyimino)ethyl]-1,3-dimethyl-2H-1,4-benzodiazepin-2-one in 150 ml of 2 N methanolic ammonia is treated with 5 g of Raney-nickel paste and the suspension is stirred in a hydrogen atmosphere for 24 hours. After filtration of the catalyst and removal of the solvent in vacuo, there is obtained 7-(1-aminoethyl)-5-(o-fluorophenyl)-1,3-dihydro-1,3-dimethyl-2H-1,4-benzodiazepin-2-one as a foam of melting point 48°–50°.

EXAMPLE 3

(a) 14.2 ml of ethyl bromide and 27.2 g of potassium carbonate are added to 13.6 b (45.9 mmol) of 7-acetyl-5-(o-fluorophenyl)-1,3-dihydro-2H-1,4-benzodiazepin-2-one in 400 ml of acetone. The mixture is stirred at room temperature for 71 hours, filtered and evaporated in vacuo. The residue is taken up in methylene chloride, the organic phase is washed with water, dried and evaporated. From methylene chloride/cyclohexane there is obtained 7-acetyl-1-ethyl-5-(o-fluorophenyl)-1,3-dihydro-2H-1,4-benzodiazepin-2-one of melting point 154°–156°.

(b) A solution of 13.0 g (40.1 mmol) of 7-acetyl-1-ethyl-5-(o-fluorophenyl)-1,3-dihydro-2H-1,4-benzodiazepin-2-one and 13.0 g of hydroxylamine hydrochloride in 65 ml of pyridine and 65 ml of ethanol is left to stand at room temperature for 4 hours. The mixture is taken up in methylene chloride, washed with 2 N hydrochloric acid and water, dried and evaporated. Traces of pyridine are removed by azeotropic evaporation with toluene. The residue gives, from methylene chloride/hexane, 1-ethyl-5-(o-fluorophenyl)-1,3-dihydro-7-[1-(hydroxyimino)ethyl]-2H-1,4-benzodiazepin-2-one of melting point 236°–238°.

EXAMPLE 4

A solution of 1 g (2.95 mmol) of 1-ethyl-5-(o-fluorophenyl)-1,3-dihydro-7-[1-(hydroxyimino)ethyl]-2H-1,4-benzodiazepin-2-one in 150 ml of ethanol is stirred with 1.0 g of Raney-nickel paste for 21 hours in a hydrogen atmosphere at 50°. After filtration over Digalite and evaporation in vacuo, there is obtained 7-(1-aminoethyl)-1-ethyl-5-(o-fluorophenyl)-1,3-dihydro-2H-1,4-benzodiazepin-2-one of melting point 53°–55°.

EXAMPLE 5

372 mg (5.91 mmol) of sodium cyanoborohydride and 1 drop of 1 percent ethanolic bromocresol solution are added to a suspension, cooled at room temperature, of 3.0 g (7.85 mmol) of 1-ethyl-5-(o-fluorophenyl)-1,3-dihydro-7-[1-(hydroxyimino)ethyl]-2H-1,4-benzodiazepin-2-one in 30 ml of methanol. Subsequently, 30 ml of 2 N methanolic hydrochloric acid are added dropwise thereto in the course of 30 minutes so that the yellow colour of the mixture is preserved. The mixture is stirred at room temperature for 48 hours, a further 372 mg of sodium cyanoborohydride being added after 24 hours. The mixture is concentrated in vacuo and the residue is adjusted to pH 10 with 6 N sodium hydroxide. After extraction with chloroform, the organic phase is washed with water, dried and evaporated. The residue gives, from ether, 1-ethyl-5-(o-fluorophenyl)-1,3,4,5-tetrahydro-7-[1-(hydroxyimino)ethyl-2H-1,4-benzodiazepin-2-one of melting point 237°–239°.

EXAMPLE 6

To a solution, stirred at room temperature, of 7.98 ml of ethanolamine in 140 ml of methanol and 9.0 ml of 5 MN methanolic hydrochloric acid are added 7.0 g (21.7 mmol) of 7-acetyl-1-ethyl-5-(o-fluorophenyl)-1,3-dihydro-2H-1,4-benzodiazepin-2-one, followed by 959 mg of sodium cyanoborohydride. The mixture is stirred under argon at room temperature for 168 hours, with 959 mg of sodium cyanoborohydride being added after 48 hours and after 144 hours. After removing the solvent in vacuo, the residue is adjusted to pH 10 with 6 N sodium hydroxide and extracted with chloroform. After washing the organic phase with water, drying and evaporating, the residue is chromatographed on 200 g of silica gel using chloroform as the elution agent. There is obtained 1-ethyl-5-(o-fluorophenyl)-1,3,4,5-tetrahydro-7-/1-[(2-hydroxyethyl)-amino]ethyl/-2H-1,4-benzodiazepin-2-one of melting point 49°–50°.

EXAMPLE 7

(a) To a solution, stirred at room temperature, of 9.1 ml of dimethylamine in 140 ml of methanol and 0.1 ml of 5 N methanolic hydrochloric acid are added 7.0 g (21.7 mmol) of 7-acetyl-1-ethyl-5-(o-fluorophenyl)-1,3-dihydro-2H-1,4-benzodiazepin-2-one, followed by 0.24 g of sodium cyanoborohydride. The mixture is stirred at room temperature for 14 days, with 924 mg of sodium cyanoborohydride being added after 2 days and after 7 days. The solvent is removed in vacuo and the residue is adjusted to pH 10 with 10 N sodium hydroxide and then taken up in chloroform. The organic phase is washed with water, dried and evaporated. The residue is chromatographed on 200 g of silica gel using chloroform as the elution agent and there is obtained 7-[1-(dimethylamino)ethyl]-1-ethyl-5-(o-fluorophenyl)-1,3,4,5-tetrahydro-2H-1,4-benzodiazepin-2-one as an oil.

(b) A solution of 2.32 g of the thus-obtained product in 50 ml of ether is treated in the cold with gaseous hydrogen chloride. The precipitated material is filtered off, washed with ether and dried in vacuo. There is obtained 7-[1-(dimethylamino)ethyl]-1-ethyl-5-(o-fluorophenyl)-1,3,4,5-tetrahydro-2H-1,4-benzodiazepin-2-one dihydrochloride of melting point 160°.

EXAMPLE 8

(a) 12.7 g (39.2 mmol) of 7-acetyl-1-ethyl-5-(o-fluorophenyl)-1,3-dihydro-2H-1,4-benzodiazepin-2-one in 240 ml of methanol are treated in the cold while stirring with 743 mg (19.6 mmol) of sodium borohydride. The mixture is subsequently stirred at room temperature for 17 hours, treated with water and then with 2 N sulphuric acid and extracted with methylene chloride. The organic phase is washed with water, dried and evaporated. The residue is chromatographed on 500 g of silica gel using ethyl acetate/toluene (1:1) as the elution agent, and gives, from cyclohexane, 1-ethyl-5-(o-fluorophenyl)-1,3-dihydro-7-(1-hydroxyethyl)-2H-1,4-benzodiazepin-2-one of melting point 55°–57°.

(b) A solution of 3.0 g (9.2 mmol) of 1-ethyl-5-(o-fluorophenyl)-1,3-dihydro-7-(1-hyroxyethyl)-2H-1,4-benzodiazepin-2-one in 10 ml of pyridine and 10 ml of acetic anhydride is left to stand at room temperature overnight and concentrated in vacuo. The residue is taken up in methylene chloride and the organic phase is washed with water, dried and evaporated. There is thus obtained 1-[1-ethyl-5-(o-fluorophenyl)-2,3-dihydro-2-oxo-1H-1,4-benzodiazepin-7-yl]ethyl acetate as a thin-layer chromatographically uniform oil.

EXAMPLE 9

(a) A mixture of 3 g (9.2 mmol) of 1-ethyl-5-(o-fluorophenyl)-1,3-dihydro-7-(1-hydroxyethyl)-2H-1,4-benzodiazepin-2-one, 4.7 ml of dimethylaniline and 1.4 ml of chlorodimethyl ether is left to stand under argon at 50° for 1 hour and at room temperature for 4 days. The mixture is made acid at 0° C. with 1 N hydrochloric acid, extracted with chloroform/ethanol (9:1) and the organic phase is washed with water. After drying and evaporating, the residue is chromatographed on 100 g of silica gel using chloroform as the elution agent. There is obtained 1-ethyl-5-(o-fluorophenyl)-1,3-dihydro-7-[1-(methoxymethoxy)ethyl]-2H-1,4-benzodiazepin-2-one as an oil.

(b) Dry gaseous hydrogen chloride is conducted into a solution of the thus-obtained product in 100 ml of ether. The precipitated material is filtered off, washed with ether and dried in vacuo. There is obtained 1-ethyl-5-(o-fluorophenyl)-1,3-dihydro-7-[1-(methoxymethoxy)ethyl]-2H-1,4-benzodiazepin-2-one hydrochloride.

EXAMPLE 10

A solution of 2.0 g (6.12 mmol) of 1-ethyl-5-(o-fluorophenyl)-1,3-dihydro-7-(1-hydroxyethyl)-2H-1,4-benzodiazepin-2-one and 0.5 ml of N-phenyl-isocyanate in 35 ml of benzene is heated to boiling under reflux for 50 hours, with 1 ml of triethylamine being added after 20 hours and after 35 hours. The mixture is evaporated in vacuo and the residue is diluted with water and extracted with chloroform/ethanol (9:1). The organic phase is washed with water, dried and evaporated. The residue is chromatographed on 100 g of silica gel using chloroform/ethanol (98:2) as the elution agent and gives, from cyclohexane, 1-[1-ethyl-5-(o-fluorophenyl)-2,3-dihydro-2-oxo-1H-1,4-benzodiazepin-7-yl]ethyl-carboxanilide of melting point 83°–85°.

EXAMPLE 11

From 2 g (6.12 mmol) of 1-ethyl-5-(o-fluorophenyl)-1,3-dihydro-7-(1-hydroxyethyl)-2H-1,4-benzodiazepin-2-one and 0.7 ml of N-butyl-isocyanate there is obtained in analogy to Example 10, after recrystallisation from cyclohexane, 1-[1-ethyl-5-(o-fluorophenyl)2,3-dihydro-2-oxo-1H-1,4-benzodiazepin-7-yl]ethyl-butylcarbamate of melting point 48°–50°.

EXAMPLE 12

(a) 42.3 g (0.41 mol) of α-amino-isobutyric acid and 50 ml (0.68 mol) of thionyl chloride in 400 ml of tetrahydrofuran are vigorously stirred at room temperature for 24 hours, treated with 100 g (0.38 mol) of 2-amino-5-nitro-2'-fluorobenzophenone and stirred at room temperature for a further 108 hours. The mixture is concentrated in vacuo, poured into 500 ml of 10 percent, ice-cold sodium bicarbonate solution and extracted with methylene chloride. After washing the organic phase with sodium bicarbonate solution and water, the solvent is removed in vacuo and the residual, crude 2-amino-2'-(o-fluorobenzoyl)-2-methyl-4'-nitropropionanilide is processed directly.

(b) 184 g of the above crude product in 1 l of toluene and 100 ml of glacial acetic acid are heated to reflux for 21 hours in a water-separator and subsequently evaporated to dryness in vacuo. The residue is slurried in 500 ml of boiling ether and filtered off. There is obtained 5-(o-fluorophenyl)-1,3-dihydro-3,3-dimethyl-7-nitro-2H-1,4-benzodiazepin-2-one of melting point 241°.

(c) From 122.3 g (0.37 mol) of 5-(o-fluorophenyl)-1,3-dihydro-3,3-dimethyl-7-nitro-2H-1,4-benzodiazepin-2-one there is obtained in analogy to paragraph (d) of Example 1, after recrystallisation from ethyl acetate, 7-amino-5-(o-fluorophenyl)-1,3-dihydro-3,3-dimethyl-2H-1,4-benzodiazepin-2-one of melting point 229°–231°.

(d) From 56.62 g (0.19 mol) of 7-amino-5-(o-fluorophenyl)-1,3-dihydro-3,3-dimethyl-2H-1,4-benzodiazepin-2-one there is obtained in analogy to paragraph (e) of Example 1 5-(o-fluorophenyl)-2,3-dihydro-3,3-dimethyl-2-oxo-1H-1,4-benzodiazepine-7-diazonium tetrafluoroborate of melting point 203°.

(e) From 90 g (0.185 mol) of 5-(o-fluorophenyl)-2,3-dihydro-3,3-dimethyl-2-oxo-1H-1,4-benzodiazepine-7-diazonium tetrafluoroborate there is obtained in analogy to paragraph (f) of Example 1, after recrystallisation from cyclohexane, 5-(o-fluorophenyl)-1,3-dihydro-7-iodo-3,3-dimethyl-2H-1,4-benzodiazepin-2-one of the melting point 202°.

(f) From 66.3 g (0.162 mol) of 5-(o-fluorophenyl)-1,3-dihydro-7-iodo-3,3-dimethyl-2H-1,4-benzodiazepin-2-one there is obtained in analogy to paragraph (g) of Example 1, after recrystallisation from cyclohexane, 5-(o-fluorophenyl)-2,3-dihydro-3,3-dimethyl-2-oxo-1H-1,4-benzodiazepine-7-carbonitrile of melting point 212°.

(g) From 33.74 g (0.169 mol) of 5-(o-fluorophenyl)-2,3-dihydro-3,3-dimethyl-2-oxo-1H-1,4-benzodiazepine-7-carbonitrile there is obtained in analogy to paragraph (h) of Example 1 7-acetyl-5-(o-fluorophenyl)-1,3-dihydro-3,3-dimethyl-2H-1,4-benzodiazepin-2-one of melting point 206°.

(h) From 9.20 g (25.28 mmol) of 7-acetyl-5-(o-fluorophenyl)-1,3-dihydro-3,3-dimethyl-2H-1,4-benzodiazepin-2-one there is obtained in analogy to paragraph (i) of Example 1, after recrystallisation from cyclohexane, 7-acetyl-5-(o-fluorophenyl)-1,3-dihydro-1,3,3-trimethyl-2H-1,4-benzodiazepin-2-one of melting point 59°.

(i) A solution of 13.66 g (40.37 mmol) of 7-acetyl-5-(o-fluorophenyl)-1,3-dihydro-1,3,3-trimethyl-2H-1,4-benzodiazepin-2-one and 13.6 g (0.196 mol) of hydroxylamine hydrochloride in 50 ml of pyridine is stirred at room temperature for 18 hours, then poured on to ice and extracted with methylene chloride/ethanol (9:1). The organic phase is washed successively with 3 N hydrochloric acid and water, dried and evaporated. The residue is chromatographed on 150 g of silica gel using methylene chloride as the elution agent and there is obtained, from ether, 5-(o-fluorophenyl)-1,3-dihydro-7-[1-(hydroxyimino)-ethyl]-1,3,3-trimethyl-2H-1,4-benzodiazepin-2-one of melting point 199°.

EXAMPLE 13

2.5 g of Raney-nickel paste are added to a solution of 2.22 g (6.28 mmol) of 5-(o-fluorophenyl)-1,3-dihydro-7-[1-(hydroxyimino)ethyl]-1,3,3-trimethyl-2H-1,4-benzodiazepin-2-one in 100 ml of 2 N methanolic ammonia and the mixture is stirred at room temperature for 24 hours in a hydrogen atmosphere. The catalyst is filtered off and the solvent is concentrated in vacuo. After filtration over 50 g of silica gel using chloroform as the elution agent, the residue gives 7-(1-aminoethyl)-5-(o-fluorophenyl)-1,3-dihydro-1,3,3-trimethyl-2H-1,4-benzodiazepin-2-one as a foam of melting point 50°–51°.

EXAMPLE 14

(a) 2.3 g (6.8 mmol) of 7-(1-aminoethyl)-5-(o-fluorophenyl)-1,3-dihydro-1,3,3-trimethyl-2H-1,4-benzodiazepin-2-one in 150 ml of dichloroethane are brought into solution under reflux. This solution is added dropwise while cooling with ice and stirring to a solution of 2 g of phosgene in 70 ml of dichloroethane so that the temperature of the mixture does not exceed 20°. Subsequently, the mixture is heated to boiling under reflux for 1 hour. Subsequently, 100 ml of dichloroethane are distilled off and the mixture is treated with 50 ml of fresh solvent. While cooling with ice, an argon stream is conducted into the solution until this has reached a temperature of 10°. There is thus obtained a solution of 7-(1-aminoethyl)-5-(o-fluorophenyl)-1,3-dihydro-1,3,3-trimethyl-2H-2-oxo-1,4-benzodiazepin-7-yl]-isocyanate.

(b) A suspension of 2.16 g of sodium carbonate in 1.25 ml of ethanolamine and 50 ml of acetonitrile is added in one portion to the above solution of the isocyanate and stirred at room temperature for 20 hours. The solvent is subsequently removed in vacuo and the residue is taken up in methylene chloride/ethanol (4:1). The organic phase is washed with water, dried and evaporated. The residue is filtered over 30 g of silica gel while washing with chloroform and there is obtained 1-/1-[5-(o-fluorophenyl)-2,3-dihydro-1,3,3-trimethyl-2-oxo-1H-1,4-benzodiazepin-7-yl]ethyl/-3-(2-hydroxyethyl)urea as a foam of melting point 83°.

EXAMPLE 15

(a) From 7.53 g (22.25 mmol) of 7-acetyl-5-(o-fluorophenyl)-1,3-dihydro-1,3,3-trimethyl-2H-1,4-benzodiazepin-2-one there is obtained in analogy to Example 8a 5-(o-fluorophenyl)-1,3-dihydro-7-(1-hydroxyethyl)-1,3,3-trimethyl-2H-1,4-benzodiazepin-2-one of melting point 68°.

(b) A solution of 2.5 g (7.34 mmol) of 5-(o-fluorophenyl)-1,3-dihydro-7-(1-hydroxyethyl)-1,3,3-trimethyl-2H-1,4-benzodiazepin-2-one in 10 ml of acetic acid anhydride and 10 ml of pyridine is left to stand at room temperature for 24 hours and then concentrated in vacuo. The residue is taken up in chloroform and the organic phase is washed successively with 2 N hydrochloric acid, 2 N sodium bicarbonate solution and water, dried and evaporated. The residue is chromatographed on 50 g of silica gel using chloroform as the elution agent. There is obtained 1-[5-(o-fluorophenyl)-2,3-dihydro-1,3,3-trimethyl-2-oxo-1H-1,4-benzodiazepin-7-yl]ethyl acetate as an oil.

EXAMPLE 16

(a) A solution of 2.9 g (42 mmol) of sodium nitrite in 7 ml of water is added while stirring to a solution, cooled in ice, of 11 g (38.8 mmol) of 7-amino-5-(o-fluorophenyl)-1,3-dihydro-1-methyl-2H-1,4-benzodiazepin-2-one in 50 ml of water and 100 ml of 50 percent aqueous hydrofluoboric acid so that the sodium nitrite solution enters below the surface of the mixture (addition time ca 15 minutes). The mixture is stirred at 5° for a further 30 minutes and then left to stand at −24° for 22 hours. The precipitated crystals are filtered off, washed with isopropanol and ether and dried at 14 Torr and room temperature. There is obtained 5-(o-fluorophenyl)-2,3-dihydro-1-methyl-2-oxo-1H-1,4-benzodiazepine-7-diazonium tetrafluoroborate (1:2) of melting point 120°–125°.

(b) 1.34 g (15 mmol) of copper (I) cyanide and 0.98 g (10 mmol) of potassium acetate are added to a solution of 1.675 g (3.6 mmol) of the diazonium salt prepared under (a) and 33 mg (0.12 mmol) of 18-crown-6 in 25 ml of N-methyl-pyrrolidone and the mixture is stirred at room temperature for 4 hours with the exclusion of light. After adding 60 ml of water, the residue is filtered off and taken up in 100 ml of ethylenediamine/water (1:1) and 150 ml of dichloromethane. The separated amine-water phase is extracted with 150 ml of dischloromethane. The organic phases are washed with water, dried and evaporated. The residue is chromatographed on 50 g of silica gel using chloroform as the elution agent, there being obtained, from cyclohexane, 5-(o-fluorophenyl)-2,3-dihydro-1-methyl-2-oxo-1H-1,4-benzodiazepine-7-carbonitrile of melting point 177°.

(c) 36.5 g (0.08 mol) of 5-(o-fluorophenyl)-2,3-dihydro-1-methyl-2-oxo-1H-1,4-benzodiazepine-7-carbonitrile, dissolved in 2700 ml of methanol and 270 ml of ammonia, are hydrogenated in an autoclave with 36.5 g of Raney-nickel at 50° and 3.5 atmospheres. The catalyst is filtered off and the solvent is removed in vacuo. There is obtained 7-(aminomethyl)-5-(o-fluorophenyl)-1,3-dihydro-1-methyl-2H-1,4-benzodiazepin-2-one as a foam.

EXAMPLE 17

From 7 g (23.5 mmol) of 7-(aminoethyl)-5-(o-fluorophenyl)-1,3-dihydro-1-methyl-2H-1,4-benzodiazepin-2-one there is obtained in analogy to Example 14, via [5-(o-fluorophenyl)-2,3-dihydro-1-methyl-2-oxo-1H-1,4-benzodiazepin-7-yl]methyl/isocyanate, the desired 1-/[5-(o-fluorophenyl)-2,3-dihydro-1-methyl-2-oxo-1H-1,4-benzodiazepin-7-yl]methyl/-3-(2-hydroxyethyl)urea as a foam of melting point 125°.

EXAMPLE 18

From 7 g (22.6 mmol) of 7-(aminoethyl)-5-(o-fluorophenyl)-1,3-dihydro-1-methyl-2H-1,4-benzodiazepin-2-one and pyrrolidine, in place of ethanolamine, there is obtained in analogy to Example 14, via /[5-(o-fluorophenyl)-2,3-dihydro-1-methyl-2-oxo-1H-1,4-benzodiazepin-7-yl]methyl/-1-isocyanate, the desired N-/[5-(o-fluorophenyl)-2,3-dihydro-1-methyl-2-oxo-1H-1,4-benzodiazepin-7-yl]methyl/-1-pyrrolidinecarboxamide as a foam of melting point 145°.

EXAMPLE 19

From 7 g (22.6 mmol) of 7-(aminoethyl)-5-(o-fluorophenyl)-1,3-dihydro-1-methyl-2H-1,4-benzodiazepin-2-one and dimethylamine, in place of ethanolamine, there is obtained in analogy to Example 14, via /[5-(o-fluorophenyl)-2,3-dihydro-1-methyl-2-oxo-1H-1,4-benzodiazepin-7-yl]-methyl/isocyanate, the desired 3-/[5-(o-fluorophenyl)-2,3-dihydro-1-methyl-2-oxo-1H-1,4-benzodiazepin-7-yl]methyl/-1,1-dimethylurea as a foam of melting point 105°.

EXAMPLE 20

A solution of 6.0 g (20.43 mmol) of 7-cyano-1,3-dihydro-5-(o-fluorophenyl)-1-methyl-2H-1,4-benzodiazepin-2-one in 150 ml of 2 N ammonia-alkaline methanol is held at 50°–60° for 3 days in a hydrogen atmosphere with 6.0 of Raney-nickel paste. After filtration of the catalyst, the solvent is removed in vacuo. The residue, dissolved in 50 ml of methylene chloride, is treated with 2.0 ml of butyl isocyanate, left to stand at room temperature for 4 days and diluted with methylene chloride. The organic phase is washed with water, dried and evaporated. The residue is chromatographed on 100 g of silica gel using chloroform as the elution agent. From ethyl acetate there is obtained 1-butyl-3-/[4-(butylcarbamoyl)-5-(o-fluorophenyl)-2,3,4,5-tetrahydro-1-methyl-2-oxo-1H-1,4-benzodiazepin-7-yl]methyl/urea of melting point 172°.

EXAMPLE 21

From 1,3-dihydro-7-nitro-5-phenyl-2H-1,4-benzodiazepin-2-one there is obtained in analogy to paragraphs (d), (e), (f) and (g) of Example 1 2,3-dihydro-2-oxo-5-phenyl-1H-1,4-benzodiazepine-7-carbonitrile which, after treatment with methyl iodide and potassium carbonate in analogy to paragraph (i) of Example 1, gives 2,3-dihydro-1-methyl-2-oxo-5-phenyl-1H-1,4-benzodiazepin-7-carbonitrile. Hydrogenation with Raney-nickel under the same conditions as those described in Example 16c gives, after recrystallisation from ether, 7-(aminomethyl)-1,3-dihydro-1-methyl-5-phenyl-2H-1,4-benzodiazepin-2-one of melting point 230° (decomposition).

EXAMPLE 22

From 7 g (25 mmol) of 7-(aminomethyl)-1,3-dihydro-1-methyl-5-phenyl-2H-1,4-benzodiazepin-2-one there is obtained in analogy to Example 14, via [(2,3-dihydro-1-methyl-2-oxo-5-phenyl-1H-1,4-benzodiazepin-7-yl)methyl]-isocyanate, after recrystallisation from ethanol, the desired 1-[(2,3-dihydro-1-methyl-2-oxo-5-phenyl-1H-1,4-benzodiazepin-7-yl)methyl]-3-(2-hydroxyethyl)urea of melting point 201°.

EXAMPLE A

1-Ethyl-5-(o-fluorophenyl)-2,3-dihydro-7-[(1-methoxymethoxy)ethyl]-2H-1,4-benzodiazepin-2-one can be used as follows as the active substance for the production of pharmaceutical preparations:

| (a) Tablets | 1 tablet contains |
|---|---|
| Active substance | 200 mg |
| Microcrystalline cellulose | 155 mg |
| Maize starch | 25 mg |
| Talc | 25 mg |
| Hydroxypropylmethylcellulose | 20 mg |
| | 425 mg |

The active substance is mixed with half of the microcrystalline cellulose and granulated with a 10 percent solution of hydroxypropylmethylcellulose in a mixture of isopropanol and methylene chloride. The granulate is dried, sieved and mixed with the remainder of the adjuvants. The mixture is then pressed on a press to biplanar tablets having a diameter of 12 mm and a break-bar.

| (b) Capsules | 1 capsule contains |
|---|---|
| Active substance | 100.0 mg |
| Maize starch | 20.0 mg |
| Lactose | 95.0 mg |
| Talc | 4.5 mg |
| Magnesium stearate | 0.5 mg |
| | 220.0 mg |

The active substance is mixed with the adjuvants and sieved. After renewed mixing, the capsule fill mass obtained is filled into interlocking gelatin capsules of suitable size on a fully automatic capsule filling machine.

What is claimed:

1. A compound of the formula

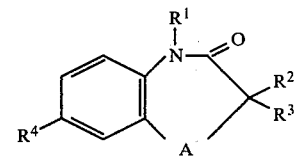

wherein A is the group

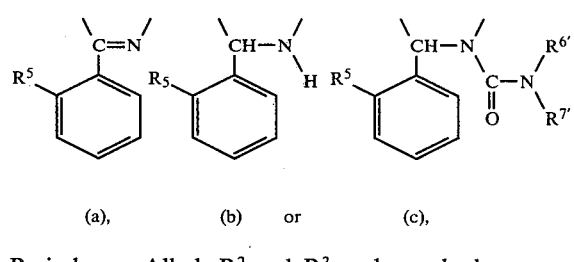

(a), (b) or (c), $R_1$ is lower Alkyl, $R^2$ and $R^3$ each are hydrogen or lower alkyl, $R^4$ is the group

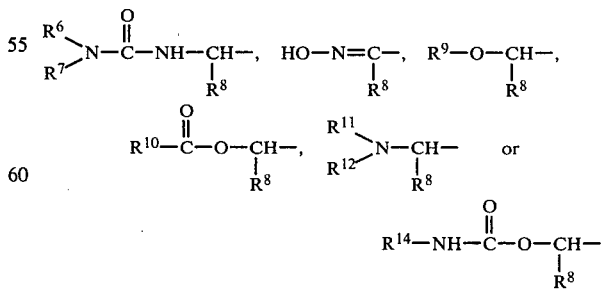

$R^5$ is hydrogen or halogen, $R^8$ is hydrogen or lower alkyl, $R^9$ is lower alkyl or lower alkoxyalkyl, $R^{10}$ is lower alkyl, $R^{11}$ is hydrogen, lower alkyl or lower hydroxyalkyl, $R^{12}$ is hydrogen or lower alkyl and $R^{14}$ is lower alkyl or phenyl optionally substituted by lower alkyl, halogen, nitro, or lower alkoxy, and either $R^6$ is hydrogen or lower alkyl and $R^7$ is lower alkyl or lower hydroxyalkyl or $R^6$ and $R^7$ together with the nitrogen atom are a 3- to 7-membered heterocycle which, when it is at least 5-membered, can contain as a ring member an oxygen or sulfur atom or a group of the formula >N-$R^{13}$, in which $R^{13}$ is hydrogen or lower alkyl, and either $R^{6'}$ is hydrogen or lower alkyl and $R^{7'}$ is lower alkyl or $R^{6'}$ and $R^{7'}$ together with the nitrogen atom are a 3- to 7-membered heterocycle which, when it is at least 5-membered, can contain as a ring member an oxygen or sulfur atom or a group of the formula >N-$R^{13'}$, in which $R^{13'}$ is lower alkyl, with the proviso that $R^4$ is the group $R^{6'}R^{7'}$N-CO-NH-CH($R^8$)-when A is the group (c), and pharmaceutically acceptable acid addition salts thereof.

2. The compound of claim 1, wherein either $R^1$ and $R^2$ both are methyl or $R^1$ is ethyl and $R^2$ is hydrogen when $R^3$ is hydrogen, $R^4$ is the group HO—N=C(CH$_3$)—A is the group (a) and $R^5$ is fluorine.

3. The compound of claim 1, wherein $R^2$ and $R^3$ both are lower alkyl when $R^4$ is the group HO—N=C($R^8$)— and A is the group (a).

4. The compound of claims 1, 2 or 3, wherein A is the group (a) or (b), $R^1$ is methyl or ethyl, $R^2$ and $R^3$ are hydrogen or methyl, $R^4$ is the group $R^6R^7$N—CO—N—H—CH($R^8$)—, HO—N=C($R^8$)—, $R^9$—O—CH($R^8$) or $R^{11}R^{12}$N—CH($R^8$)—, $R^5$ is hydrogen or fluorine and $R^8$ is hydrogen or methyl.

5. The compound: 1-ethyl-5-(o-fluorophenyl)-1,3-dihydro-7-[1-(methoxymethoxy)-ethyl]-2H, 1,4-benzodiazepin-2-one.

6. The compound: 1-ethyl-5-(o-fluorophenyl)-1,3,4,5-tetrahydro-7-[1-hydroxyimino)-ethyl]-2H-1,4-benzodiazepin-2-one.

7. The compound: 1-ethyl-5-(o-fluorophenyl)-1,3,4,5-tetrahydro-7/1-[2-hydroxyethyl)-amino]ethyl-2H-1,4-benzodiazepin-2-one.

8. The compound: 7-[1-(dimethylamino)ethyl]-1-ethyl-5-(o-fluorophenyl)-1,3,4,5-tetrahydro-2H-1,4-benzodiazepin-2-one.

9. The compound: 7-(1-aminoethyl)-5-(o-fluorophenyl)-1,3-dihydro-1,3-dimethyl-2H-1,4-benzodiazepin-2-one.

10. The compound: 1-[(2,3-dihydro-1-methyl-2-oxo-5-phenyl-1H-1,4-benzodiazepin-7-yl)methyl]-3-(2-hydroxyethyl)urea.

11. A compound of the formula

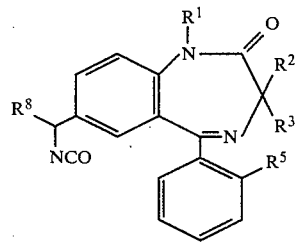

V wherein $R^1$ is lower alkyl, $R^2$ and $R^3$ each are hydrogen or lower alkyl, $R^5$ is hydrogen or halogen and $R^8$ is hydrogen or lower alkyl.

12. A process for the manufacture of a compound of the formula

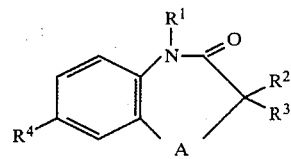

I wherein A is the group

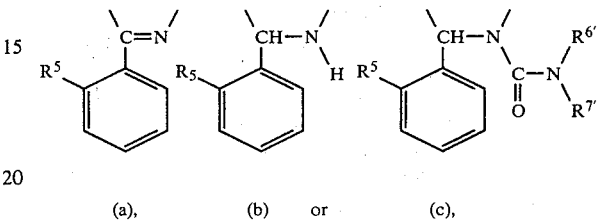

(a), (b) or (c), $R^1$ is lower alkyl, $R^2$ and $R^3$ each are hydrogen or lower alkyl, $R^4$ is the group

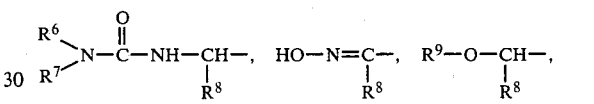

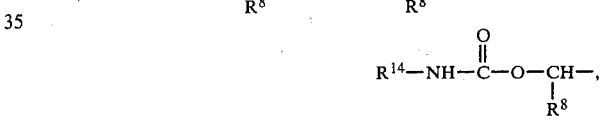

$R^5$ is hydrogen or halogen, $R^8$ is hydrogen or lower alkyl, $R^9$ is lower alkyl or lower alkoxyalkyl, $R^{10}$ is lower alkyl, $R^{11}$ is hydrogen, lower alkyl or lower hydroxyalkyl, $R^{12}$ is hydrogen or lower alkyl and $R^{14}$ is lower alkyl or aryl, and either $R^6$ is hydrogen or lower alkyl and $R^7$ is lower alkyl or lower hydroxyalkyl or $R^6$ and $R^7$ together with the nitrogen atom are a 3- to 7-membered heterocycle which, when it is at least 5-membered, can contain as a ring member an oxygen or sulfur atom or a group of the formula N-$R^{13}$, in which $R^{13}$ is hydrogen or lower alkyl, and either $R^{6'}$ is hydrogen or lower alkyl and $R^{7'}$ is lower alkyl or $R^{6'}$ and $R^{7'}$ together with the nitrogen atom are a 3- to 7-membered heterocyclic which, when it is at least 5-membered, can contain as a ring member an oxygen or sulfur atom or a group of the formula N-$R^{13'}$, in which $R^{13'}$ is lower alkyl, with the proviso that $R^4$ is the group $R^{6'}R^{7'}$N—CO—NH—CH($R^8$)— when A is the group (c), and pharmaceutically acceptable acid addition salts thereof, which process comprises (a) reducing a nitrile of the formula

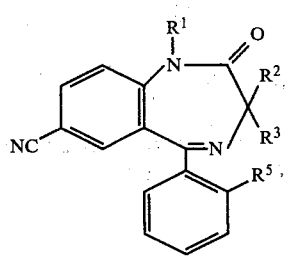

wherein $R^1$, $R^2$, $R^3$ and $R^5$ are as above to the corresponding primary amine, or (b) treating a carbonyl compound of the formula

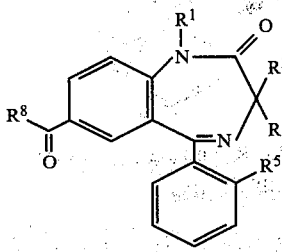

wherein $R^1$, $R^2$, $R^3$, $R^5$ and $R^8$ are as above, with hydroxylamine, or (c) reacting a carbonyl compound of the above formula III with an amine of the formula

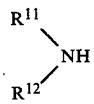

wherein $R^{11}$ and $R^{12}$ are as above, and a reducing agent, or (d) monoalkylating or dialkylating the primary amino group in a compound of the formula

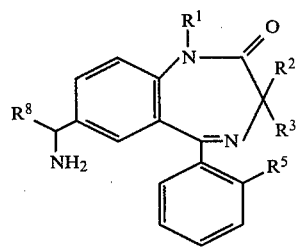

wherein $R^1$, $R^2$, $R^3$, $R^5$ and $R^8$ are as above, or (e) reducing an oxime of the formula

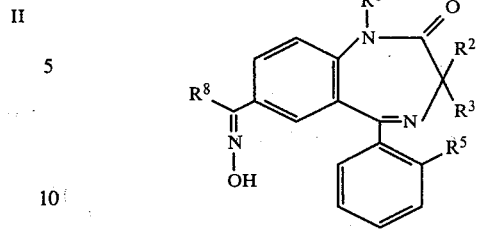

wherein $R^1$, $R^2$, $R^3$, $R_5$ and $R^8$ are as above,
to the corresponding primary amine, or (f) reacting an isocyanate of the formula

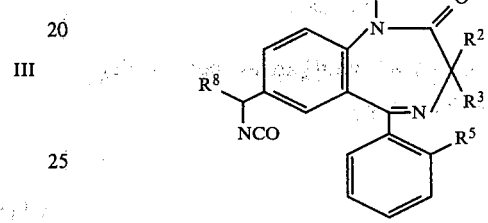

wherein $R^1$, $R^2$, $R^3$, $R^5$ and $R^8$ are as above, with an amine of the formula

wherein $R^6$ and $R^7$ are as above or (g) reacting an amine of the formula

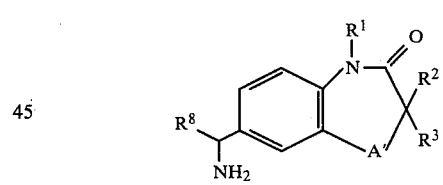

wherein A' is the group (a) or (b) above and $R^1$, $R^2$, $R^3$ and $R^8$ are as above, with a halide of the formula

wherein X is halogen, and either $R^{6''}$ and $R^{7''}$ each are lower alkyl or $R^{6''}$ and $R^{7''}$ together with the nitrogen atom are a 3-to 7-membered heterocycle which, when it is at least 5-membered, can contain as a ring member an oxygen or sulfur atom or a group of the formula $>N-R^{13'}$, in which $R^{13'}$ is lower alkyl, or (h) reacting an amine of the above formula Ib with an isocyanate of the formula R<sup>7'''</sup>—NCO  VIII wherein R<sup>7'''</sup> is lower alkyl,
or
(i) etherifying an alcohol of the formula $$\text{[structure IX: benzodiazepine with } R^1, R^2, R^3, R^5, R^8\text{-CH}_2\text{OH]}$$

IX wherein $R^1$, $R^2$, $R^3$, $R^5$ and $R^8$ are as above, with a compound of the formula R<sup>9</sup>—L   X wherein R<sup>9</sup> is as above and L is a leaving group,
or
(j) reacting an alcohol of the above formula IX with an agent which yields a group of the formula $$R^{10}\text{—}\overset{\overset{\displaystyle O}{\|}}{C}\text{—}$$

XI wherein R<sup>10</sup> is as above,
or
(k) reacting an alcohol of the above formula IX with an isocyanate of the formula R<sup>14</sup>—NCO   XII wherein R<sup>14</sup> is as above,
or
(l) reducing an amino compound of the formula $$\text{[structure Ic: benzodiazepine with } R^1, R^2, R^3, R^4, R^5\text{]}$$

Ic wherein $R^1$, $R^2$, $R_3$, $R^4$ and $R^5$ are as above, to the corresponding amine,
or
(m) converting a compound of formula I into a pharmaceutically acceptable acid addition salt.

* * * * *